United States Patent [19]

Johansen

[11] 4,341,867

[45] Jul. 27, 1982

[54] PROCESS FOR RECOVERING ENZYMES FROM BLOOD

[75] Inventor: Jack T. Johansen, Rungsted Kyst, Denmark

[73] Assignee: De Forende Bryggerier A/S, Copenhagen, Denmark

[21] Appl. No.: 149,393

[22] Filed: May 13, 1980

[30] Foreign Application Priority Data

Apr. 21, 1980 [DK] Denmark ............................ 1688/80

[51] Int. Cl.³ .......................... C12N 9/02; C12N 9/08; C12N 9/88
[52] U.S. Cl. ................................... 435/189; 435/192; 435/232; 435/259; 435/816
[58] Field of Search ............... 435/189, 192, 232, 259, 435/183, 814, 815, 816

[56] References Cited

U.S. PATENT DOCUMENTS 3,579,495 5/1971 Huber ............................ 260/113 X
3,763,137 10/1973 Huber et al. ........................ 260/113

FOREIGN PATENT DOCUMENTS 478097 10/1969 Switzerland .
720232 12/1954 United Kingdom .
1532848 11/1978 United Kingdom .

OTHER PUBLICATIONS

Ku et al., *Journal of Pharmaceutical Science*, 1974, vol. 63, No. 1, pp. 60–64.

Briggs et al., Biochimica et Biophysica Acta, vol. 537, pp. 100–109, (1978).

*Primary Examiner*—Lionel M. Shapiro
*Attorney, Agent, or Firm*—Ladas & Parry

[57] ABSTRACT

Various enzymes, in particular Cu,Zn-superoxide dismutase (SOD), catalase and carbonic acid anhydrase, are recovered from blood by admixing wholly or partly isolated blood cells with ethanol or a homologous alcohol until a concentration of 10 to 70% by volume and allowing them to stand for hemolysis of the blood cells and denaturation of the hemoglobin, and then adding water up to the double volume or more, and removing the precipitate of cell residuals, hemoglobin and other denatured proteins from the suspension. Then the desired enzymes are isolated from the solution obtained.

In particular, SOD and catalase can both be isolated by chromatography of the solution at a pH of 4.7 to 5.5 on a cation exchange resin of the same polarity as SOD in the pH range used and elution of the resin with a buffer solution which has a pH in the range 4.7 to 7.5 and an ionic strength in the range 0.01 to 1.0 M, SOD being eluted at the lowest pH and/or the lowest ionic strength.

The process allows both the hemolysis of the blood cells and the precipitation of the hemoglobin to be carried out in one step while retaining the activity of the desired enzymes, so that they can be obtained in a high yield in a manner which lends itself to use on an industrial scale. Further, SOD and catalase may be isolated and purified in a single chromatography step.

6 Claims, No Drawings

PROCESS FOR RECOVERING ENZYMES FROM BLOOD

The present invention relates to a process for recovering one or more of the enzymes Cu,Zn superoxide dismutase, catalase and carbonic acid anhydrase from blood by lysing the blood cells and isolating the desired enzymes from the solution obtained.

Among the enzymes that may be obtained are in particular Cu,Zn-superoxide dismutase (SOD) and catalase, but also e.g. carbonic acid anhydrase may be recovered.

The Danish Patent No. 132 864 discloses a process for recovering SOD from mammal blood, particularly bovine blood, comprising the steps of lysing blood cells, freed from plasma by decanting or centrifugation, with cold deionized water, optionally containing a little surfactant, and precipitating the hemolysate with a halogenated, organic solvent, such as chloroform, in the presence of a water miscible, organic solvent, such as ethanol, or with water ammonium sulfate at a temperature below 5° C. The precipitate was washed once or several times with deionized water and the combined supernatant was heated to 60° to 65° C. in the presence of a buffer solution containing divalent metal ions having an atomic radius of 0.69 to 0.80 A to denature heat labile proteins, especially carbonic acid anhydrase. After rapid cooling below room temperature, the precipitated proteins were removed by filtration and centrifugation, and the SOD containing solution was purified by ion exchange chromatography, preparative electrophoresis and/or gel filtration. Said process is reported to give a yield of SOD of about 0.01% (weight/vol.) on the basis of packed red blood cells.

Substituting fractionation by means of $K_2HPO_4$ and acetone for the heating step in said process, and subsequently chromatographing the active part of the fractionated soluble proteins on diethylaminoethyl cellulose (DEAE cellulose) at pH 7.4 gave a yield of SOD from packed bovine blood cells of 0.006% (weight/vol.) with an activity of 3300 units/mg, corresponding to 60% of the present SOD activity.

Said multi-step processes, however, are not useful on a commercial scale, partly because of the many steps which complicate the process, partly because of the necessity of using large amounts of organic solvents and optionally $K_2HPO_4$.

According to the Danish Pat. No. 133 246 it has been attempted to eliminate precipitation of hemoglobin with chloroform and/or ethanol and fractionation with $K_2HPO_4$ and acetone to remove carbonic acid anhydrase by (a) adjusting the hemolysate to a pH value of about 6 and an ionic strength below about 0.01 M and passing the solution through a column of an ion exchange resin having slightly basic groups, preferably DEAE cellulose, to adsorb SOD on the resin, (b) washing the column with a buffer solution of the same pH and ionic strength to remove hemoglobin, and (c) eluting the adsorbed SOD from the column with an aqueous medium having a pH value of 5.7 to 6.3 and an ionic strength that increases gradually or in stepwise gradients from below about 0.02 M to above about 0.03 M, SOD being eluted from the fraction of the eluate which begins at the first ionic strength where the ratio of the absorbance values $A_{265}$ to $A_{280}$ reaches a maximum, and ends at the first ionic strength where the contents of Cu and Zn and the ratio of $A_{265}$ to $A_{280}$ decrease at the same time. This process is reported to give a yield of SOD from packed, red blood cells of 0.01 to 0.013% (weight/vol.) with an activity of 2500 units/mg or almost as much as 75% of the total original SOD activity in the hemolysate. This process, however, is not useful on a commercial scale either as it comprises chromatography of large volumes of liquid, which requires correspondingly large chromatography columns. Further, more than 99.8% of the proteins which are chromatographed are undesirable proteins, reducing the life of the column and the rate of chromatography.

In the Danish Pat. No. 134 914 precipitation of hemoglobin with chloroform/ethanol and fractionation with $K_2HPO_4$ and acetone to remove carbonic acid anhydrase are replaced by a single heating step in which the hemolysate at a pH between 5 and 8 is heated to a temperature of 60° to 80° C. to precipitate the hemoglobin as well as the carbonic acid anhydrase and the other heat labile proteins, and then the mixture is cooled, the precipitated proteins are separated and SOD is isolated from the supernatant, e.g. by precipitation with acetone or, preferably, by ion exchange chromatography on DEAE cellulose under the same conditions as in the process described in the foregoing. This of course simplifies the process, but it is nevertheless not satisfactory because a loss of SOD occurs in the heating step. The patent reports purification of 40 to 50 times after heat precipitation and a yield of SOD of 70 to 90% of what was present in the starting blood.

Briggs and Fee (Biochim. et Biophys. Acta, 537 (1978), p. 86–99) replaced the precipitations of hemoglobin and of heat labile proteins by a batch treatment of the hemolysate first with carboxymethyl cellulose (CM cellulose) at pH 6 and then with a mixed bed ion exchanger under control of pH till approximately neutral. The resultant mixture was treated with DEAE cellulose, which was transferred to a column and first washed with large amounts of 2 mM Na-phosphate buffer to elute residual hemoglobin and then eluted with 0.1 M Na-phosphate buffer and active fractions were collected. These were combined and again batch treated with a mixed bed ion exchanger and CM cellulose, respectively, to remove further accompanying proteins. The SOD containing solution was again applied to a column of DEAE cellulose and eluted with a linear gradient from 2 to 100 mM Na-phosphate buffer, and the active fractions were combined, concentrated by ultrafiltration and subjected to gel filtration on "Biogel P-100". Chromatography and gel filtration were repeated to obtain a pure preparation.

This process is totally unsuitable for use on a commercial scale as it is very complicated owing to the many steps, and as excessively large amounts of ion exchangers are to be used, thus in the first purification step 2.5 kg of CM cellulose and 0.5 kg of mixed bed ion exchanger for 2 l of hemolysate. Moreover, the yield of SOD in this process is only 21% of the theoretically obtainable one, and there is a loss of about 25% of the total SOD activity already in the CM cellulose purification step, which is no wonder in the light of the later finding on which the invention described in the copending Danish Patent Application No. 1687/80 is based, viz. that carboxymethyl cellulose can adsorb SOD completely at a pH of 4.7 to 5.5.

The only process which till now has been used in practice for recovering SOD from blood, is the one previously described, in which the hemolysate is precipitated with chloroform/ethanol, and the supernatant is subjected to fractionation with $K_2HPO_4$ and acetone, followed by chromatography of the active part on DEAE cellulose.

This generally yields about 40 mg of pure SOD per liter of packed blood cells against a theoretical yield of about 100 mg/l.

According to the invention it has now been found that it is possible to hemolyse the blood cells and precipitate the hemoglobin in one step while retaining the total SOD activity and the activity of other desired enzymes, in particular catalase and carbonic acid anhydrase, so that they may be recovered in a manner which lends itself to use on a commercial scale.

This is achieved with the process of the invention which is characterized by admixing wholly or partly isolated blood cells with an alkanol having 2 to 4 carbon atoms, preferably ethanol, until a concentration of 10 to 70% by volume and allowing them to stand for hemolysis of the blood cells and denaturation of the hemoglobin, and then adding water in an amount so as at least approximately to double the volume, removing the precipitate of cell residuals, hemoglobin and other denatured proteins from the suspension, and finally isolating the desired enzymes from the solution obtained.

The process is carried out most practically by admixing the wholly or partly isolated blood cells, e.g. blood which on standing has been freed of most of the plasma by decantation, with an equally large volume of 96% ethanol under vigorous stirring. On standing with stirring for about 1 hour the suspension is diluted to the double volume with deionized water, and stirring is continued for 30 to 60 minutes. Then the suspension is centrifuged and the cake of hemoglobin and cell residuals is washed with a little water. This produces a clear reddish solution containing i.a. SOD, catalase and carbonic acid anhydrase.

The carbonic acid anhydrase may readily be isolated from this solution by affinity chromatography on a resin that specifically adsorbs carbonic acid anhydrase, but not the other desired enzymes. An example of such a resin is the cross-linked agarose, "Sepharose" ®, substituted with glycyl-tyrosine-azobenzenesulfonamide groups. Following washing of the resin the carbonic acid anhydrase may be eluted with an aqueous potassium thiocyanate solution as described by J. T. Johansen (Carlsberg Research Communications Vol. 41, 73–81 (1976)).

The solution from which the carbonic acid anhydrase has been removed still contains SOD and catalase. According to the invention it has been found that the process for isolating SOD from aqueous solutions which is claimed in the Danish Patent Application No. 1687/80 can be used for isolating both SOD and catalase from the solution in a single step by subjecting the solution at a pH of about 4.8 to chromatography on a cation resin of the same polarity as SOD in the pH range used. SOD and catalase are best eluted from the resin with a buffer solution having a pH in the range 4.7 to 7.5 and ionic strength in the range 0.01 to 1.0 M, SOD being eluted at the lowest pH and/or the lowest ionic strength. A pH gradient and/or ionic strength gradient in these ranges may be used in a known manner so that SOD is eluted first. Preferably, SOD is eluted first with a buffer solution having a pH of 4.7 to 5.5 and an ionic strength of 0.02 to 0.2 M, and then the catalase is eluted with a buffer solution having a pH of 6.5 to 7.5 and an ionic strength of 0.1 to 1.0 M. Then the SOD and catalase containing fractions may be separately purified further in a known manner.

As examples of useful cation exchange resins in the foregoing chromatography may be mentioned carboxymethyl celluloses, such as those available under the name "CM-23", and "CM-52" from Whatman Ltd., Great Britain, and under the name "CM-Sephacel" ® from Pharmacia Fine Chemicals AB, Sweden, cross-linked dextrans substituted with carboxymethyl groups, such as the one available under the name "CM-Sephadex" ® from Pharmacia Fine Chemicals AB, cross-linked dextrans substituted with sulfopropyl groups, such as the one available under the name "SP-Sephadex" ® from Pharmacia Fine Chemicals AB and cross-linked agaroses substituted with carboxymethyl groups, such as the one available under the name "CM-Sepharose ® CL 6B" from Pharmacia Fine Chemicals AB.

After the elutions the column may be regenerated by flushing with a base, water, an acid and water and subsequent equilibration with the desired buffer.

Chromatography of the solution on a cation ion exchange resin may optionally be effected batch-wise by stirring the ion exchange granulate into the solution, but it is carried out most advantageously as a column procedure which is easier to work with on a larger scale and ensures that all the enzyme is adsorbed on the ion exchanger.

Before the further purification of the two solutions obtained, it has been found expedient to concentrate both of them by ultrafiltration at this stage.

Suitably, the SOD solution may then be subjected to diafiltration using a phosphate buffer of a low ionic strength to remove low molecular impurities.

Final purification of the SOD solution may appropriately be effected by chromatography on DEAE cellulose. This yields a clear solution from which the pure SOD may optionally be isolated in solid form by freeze drying.

It has been found that the use of the process of the invention in the manner described above will provide a yield of completely pure SOD of about 60 mg per liter of packed blood cells corresponding to about 60% of the approx. 100 mg/l which is theoretically possible.

The catalase solution may suitably be purified by fractional precipitation with ammonium sulfate.

The process of the invention will be illustrated more fully in the following example.

EXAMPLE

Hemolysis and precipitation of hemoglobin 7 liters of decanted blood that still contained about 2 l of plasma and thus corresponded to about 5 l of packed blood cells, were admixed with 7 l of 96% ethanol under vigorous stirring. After 1 hour 15 l of deionized water were added, and stirring was continued for 30 minutes.

The suspension was centrifuged in a MSE basket centrifuge at approx. 2000 rpm. and the cake of hemoglobin was washed with 2 l of water before the centrifuge was emptied. 29.5 l of supernatant were obtained.

Isolation of carbonic acid anhydrase

The supernatant was applied to a 10×12 cm column of the affinity matrix "Sepharose"-glycyl-tyrosine-azobenzenesulfonamide that specifically adsorbs carbonic acid anhydrase, but does not adsorb SOD and catalase. After washing of the affinity matrix the carbonic acid anhydrase was eluted with an aqueous 0.2 M potassium thiocyanate solution containing 0.05 M "Tris" sulfate and having a pH of 6.5.

Isolation of SOD and catalase

The solution that contained SOD and catalase was adjusted to pH 4.75 with 1 M acetic acid, and passed through a 20 cm diameter column, packed with 2 l of "CM-23" equilibrated in 20 mM Na-acetate buffer, pH 4.8. The flow rate was approx. 15 l per hour. The ion exchanger was then washed with 15 l of 20 mM Na-acetate buffer, pH 4.8.

The column was eluted with a linear gradient of 3 l of 100 mM and 3 l of 200 mM Na-acetate, pH 4.8, at a flow rate of 1.5 l per hour. SOD was eluted at about 150 mM Na-acetate.

Catalase was eluted with 0.1 M Na-phosphate buffer, pH 7.0.

The SOD and catalase containing fractions were separately pooled and ultrafiltrated on a "DDS 600" membrane in a "DDS MF cell", both available from De danske Sukkerfabriker A/S.

SOD purification

The SOD solution was diafiltrated using a 10 mM Na-phosphate buffer, pH 7.5., and further purified by chromatography on a "DE-52" column (5×8 cm), equilibrated in a 10 mM Na-phosphate buffer, pH 7.5. The column was developed with a linear gradient of 2×600 ml of 10 mM Na-phosphate buffer, pH 7.5, containing 0→0.125 M NaCl. The flow rate was 110 ml per hour, and fractions of 10 ml were collected.

The SOD containing fractions were pooled. Specific gravity and absorption spectrum showed that the enzyme was pure.

Catalase purification

The catalase solution from the ultrafiltration was purified by (NH$_4$)$_2$SO$_4$ fractionation.

Regeneration of the "CM-23" column

After elution of the catalase 3 l of 0.5 M NaOH solution were passed through the column followed by 3 l of water. Then 3 l of 0.5 M hydrochloric acid were passed through the column followed by 3 l of water and 3 l of 0.2 M Na-acetate buffer, pH 4.8.

The column was then treated with 20 mM Na-acetate buffer, pH 4.8, until the conductivity and pH of the eluate were the same as those of the buffer. The column was then ready for use again.

Results

A survey of the purification steps carried out and the yields of SOD, catalase and carbonic acid anhydrase is given in the table below.

TABLE

Isolation and purification of SOD, catalase and carbonic acid anhydrase from 5 liters of red blood cells.

| | Volume (liter) | SOD (mg) | Yield (%) | Catalase (mg) | Yield (%) | Carbonic acid anhydrase (mg) | Yield (%) |
|---|---|---|---|---|---|---|---|
| 1. 7 l of decanted blood + 7 l of ethanol | 14 | | | | | | |
| 2. Addition of 15 l of water | 29 | | | | | | |
| 3. Centrifugation and washing | 29.5 | 365 | 100 | 1600 | 100 | 11 000 | 100 |
| 4. Affinity, chromatography and elution of carbonic acid anhydrase | 2 | | | | | 10 000 | 90 |
| 5. Column "CM-23" and elution of SOD | 1.3 | 300 | 82 | | | | |
| 6. Elution of catalase | 2 | | | 1400 | 87 | | |
| 7. Ultrafiltration of SOD solution | 0.25 | 290 | 79 | | | | |
| 8. Column "DE-52" and elution | 0.30 | 290 | 79 | | | | |

I claim:

1. A process for recovery one or more of the enzymes Cu,Zn-superoxide dismutase (SOD), catalase and carbonic acid anhydrase from blood by lysing the blood cells and isolating the desired enzymes from the solution obtained, characterized by admixing wholly or partly isolated blood cells with an alkanol having 2 to 4 carbon atoms until a concentration of 10 to 70% by volume and allowing them to stand for hemolysis of the blood cells and denaturation of the hemoglobin and then adding water in an amount so as at least approximately to double the volume of the mixture, removing the precipitate of cell residuals, hemoglobin and other denatured proteins from the suspension, and finally isolating the desired enzymes from the solution obtained.

2. A process according to claim 1, characteristized by isolating one or more of the enzymes Cu,Zn-superoxide dismutase (SOD), catalase and carbonic acid anhydrase from the solution.

3. A process according to claim 2, characterized by the fact that SOD and catalase are isolated from the solution by subjecting said solution at a pH of about 4.8 to chromatography on a cation exchange resin of the same polarity as SOD in the pH range used, eluting SOD and catalase from the resin with a buffer solution which has a pH in the range 4.7 to 7.5 and an ionic strength in the range 0.01 to 1.0 M, SOD being eluted at the lowest pH and/or lowest ionic strength.

4. A process according to claim 3, characterized by eluting SOD from the cation exchange resin with a buffer solution having a pH of 4.7 to 5.5 and an ionic strength of 0.02 to 0.2 M and eluting the catalase with a buffer solution having a pH of 6.5 to 7.5 and an ionic strength of 0.1 to 1.0 M.

5. A process according to claim 3 or 4, characterized by using as cation exchange resin carboxymethyl celluloses or cross-linked dextrans substituted with carboxymethyl groups or sulfopropyl groups or cross-linked agaroses substituted with carboxymethyl groups.

6. A process according to any one of claims 1, 2, 3 and 4 wherein said alkanol is ethanol.

* * * * *